(12) United States Patent
Kim et al.

(10) Patent No.: US 11,207,264 B2
(45) Date of Patent: Dec. 28, 2021

(54) COSMETICS COMPOSITION HAVING IMPROVED WATER ABSORBABILITY AND OIL ABSORBABILITY

(71) Applicant: CQV CO., LTD., Chungcheongbuk-do (KR)

(72) Inventors: Ki-Jung Kim, Cheongju-si (KR); Sang-Hoon Kim, Cheongju-si (KR); Kwang-Choong Kang, Chungcheongbuk-do (KR); Byung-Ki Choi, Cheongju-si (KR); Kwang-Soo Lim, Cheongju-si (KR); Kil-Wan Chang, Cheongju-si (KR)

(73) Assignee: CQV CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 16/962,341

(22) PCT Filed: Dec. 24, 2019

(86) PCT No.: PCT/KR2019/018350
§ 371 (c)(1),
(2) Date: Jul. 15, 2020

(87) PCT Pub. No.: WO2020/141781
PCT Pub. Date: Jul. 9, 2020

(65) Prior Publication Data
US 2020/0337982 A1    Oct. 29, 2020

(30) Foreign Application Priority Data

Jan. 3, 2019 (KR) .................. 10-2019-0000890

(51) Int. Cl.
| | | |
|---|---|---|
| *A61K 8/891* | (2006.01) | |
| *A61K 8/19* | (2006.01) | |
| *A61K 8/25* | (2006.01) | |
| *A61K 8/26* | (2006.01) | |
| *A61K 8/27* | (2006.01) | |
| *A61K 8/28* | (2006.01) | |
| *A61K 8/29* | (2006.01) | |
| *A61Q 1/02* | (2006.01) | |
| *A61Q 5/02* | (2006.01) | |
| *A61Q 19/00* | (2006.01) | |

(52) U.S. Cl.
CPC .............. *A61K 8/891* (2013.01); *A61K 8/19* (2013.01); *A61K 8/25* (2013.01); *A61K 8/26* (2013.01); *A61K 8/27* (2013.01); *A61K 8/28* (2013.01); *A61K 8/29* (2013.01); *A61Q 1/02* (2013.01); *A61Q 5/02* (2013.01); *A61Q 19/00* (2013.01); *A61K 2800/43* (2013.01); *A61K 2800/621* (2013.01)

(58) Field of Classification Search
None
See application file for complete search history.

(56) References Cited

U.S. PATENT DOCUMENTS

2007/0253989 A1* 11/2007 Abe .................. C09C 3/10
424/401

FOREIGN PATENT DOCUMENTS

| JP | 2012-184206 A | 9/2012 |
|---|---|---|
| KR | 10-2012-0021926 A | 3/2012 |
| KR | 10-2013-0011584 A | 1/2013 |
| KR | 10-2015-0069363 A | 6/2015 |
| KR | 10-2015-0109249 A | 10/2015 |

OTHER PUBLICATIONS

JP2012184206 English Translation from Google Patents, accessed Sep. 30, 2020 (Year: 2012).*
Zhou et al. "Facile fabrication of golf ball-like hollow microspheres of organic-inorganic silica", J. Mater. Chem., 2011, 21, pp. 13056-13061. (Year: 2011).*
Fold, Definition of Fold by Merriam-Webster, accessed Apr. 13, 2021 (Year: 2021).*
International Search Report dated Apr. 17, 2020, in connection with corresponding International Patent Application No. PCT/KR2018/018350, citing the above references.
Written Opinion dated Apr. 17, 2020, in connection with corresponding International Patent Application No. PCT/KR2018/018350, citing the above references.

* cited by examiner

*Primary Examiner* — Melissa L Fisher
(74) *Attorney, Agent, or Firm* — Hauptman Ham, LLP (57) ABSTRACT

A cosmetics composition having improved water absorbability and oil absorbability is provided. The cosmetics composition effectively controls sweat and sebum, thereby making it possible to improve persistence of make-up and to keep skin from looking dull.

13 Claims, 3 Drawing Sheets

COSMETICS COMPOSITION HAVING IMPROVED WATER ABSORBABILITY AND OIL ABSORBABILITY

CROSS-REFERENCE TO RELATED APPLICATION

The present application is a national stage filing under 35 U.S.C § 371 of PCT application number PCT/KR2019/018350 filed on Dec. 24, 2019 which is based upon and claims the benefit of priorities to Korean Patent Application No. 10-2019-0000890, filed on Jan. 3, 2019, in the Korean Intellectual Property Office, which are incorporated herein in their entireties by reference.

TECHNICAL FIELD

Disclosed herein is a cosmetics composition having improved water absorbability and oil absorbability, and the cosmetics composition can effectively control sweat and sebum, thereby improving persistence of make-up and keeping skin from looking dull.

BACKGROUND

Sebum is a substance like oil produced by the sebaceous glands and preventing skin from drying out, and is a complex of lipids. Sebum includes at least seven to eight or more substances. Specifically, sebum includes triglycerides, free fatty acids, squalene, wax esters, cholesterol, linoleic acids and other substances. Sebum forms a fluid layer over the skin surface to protect skin.

However, sebum changes make-up over time. Accordingly, sebum control is crucial for persistence of make-up and prevention of dull skin.

Sweat is fluid secreted by the sweat glands to adjust human body temperature. There are two types of sweat glands: eccrine and apocrine. Secretion produced by the eccrine sweat glands is termed sweat. Sweat is composed of 99% of water, and the remaining 1% contains sodium, chlorine, potassium, nitrogen inclusions, lactic acids, urea and the like. When body temperature rises, the sweat glands secret sweat. Evaporation of sweat from the surface of the skin cools the human body. However, due to sweat, make-up becomes patchy, and the patchy makeup makes skin look dull. Lowered persistence of make-up and dull skin are problems that need to be solved.

DISCLOSURE

Technical Problems

The present disclosure is directed to a cosmetics composition that may include silicone powder having a wrinkled surface, thereby ensuring improvement in water absorbability and oil absorbability.

Aspects of the present disclosure are not limited to the above-described ones. Additionally, other aspects and advantages that have not been mentioned can be clearly understood from the following description by one having ordinary skill in the art.

Technical Solutions

According to an aspect of an embodiment, a cosmetics composition may include silicone powder having a wrinkled surface.

In a cosmetics composition according to an aspect of another embodiment, silicone powder may include polymethylsilsesquioxane (PMSQ).

According to an aspect of another embodiment, a cosmetics composition may include polymethylsilsesquioxane (PMSQ) provided with at least one coating layer on a surface thereof.

According to an aspect of another embodiment, a cosmetics composition may include 1 to 15 wt % of polymethylsilsesquioxane (PMSQ) relative to a total wt % of the cosmetics composition.

Advantageous Effects

Cosmetics formulated with the cosmetics composition according to the present disclosure may have higher water absorbability and oil absorbability than cosmetics of the related art.

Cosmetics formulated with the cosmetics composition according to the present disclosure may ensure excellent persistence of make-up.

Cosmetics formulated with the cosmetics composition according to the present disclosure may prevent oiliness and stickiness.

Cosmetics formulated with the cosmetics composition according to the present disclosure may cover skin flaws/make skin flawless and improve skin tone.

DETAILED DESCRIPTION

Advantages and features according to the present disclosure, and a method of achieving the same may be clearly understood from the following embodiments that are described with reference to the accompanying drawings. However, the present disclosure is not intended to limit the embodiments. Rather, the present disclosure is intended to cover various modifications and is provided so that it may be thorough and complete and its scope may be fully conveyed to one having ordinary skill in the art to which the disclosure pertains. The present disclosure should be defined only according to the scope of the appended claims.

Silicone powders having a wrinkled surface according to the present disclosure are described hereunder.

Particles of the silicone powders have a wrinkled surface, thereby ensuring excellent water absorbability and oil absorbability. Additionally, in case cosmetics including particles of the silicone powders having a wrinkled surface are applied on a user's skin, a light feeling of application may be provided to the user.

The silicone powders having a wrinkled surface according to the present disclosure may include polymethylsilsesquioxane (PMSQ).

The component polymethylsilsesquioxane, which is a silicone-based polymer, may be expressed as a chemical formula 1 below.

[Chemical formula 1]

chain ends    Units of the material

Polymethylsilsesquioxane, as expressed as chemical formula 1 above, is a polymer that is connected by a Si—O bond. The component polymethylsilsesquioxane polymer has a Si—CH₃ bond structure and a Si—O bond structure, thereby ensuring water absorbability and oil absorbability.

Figure 1:
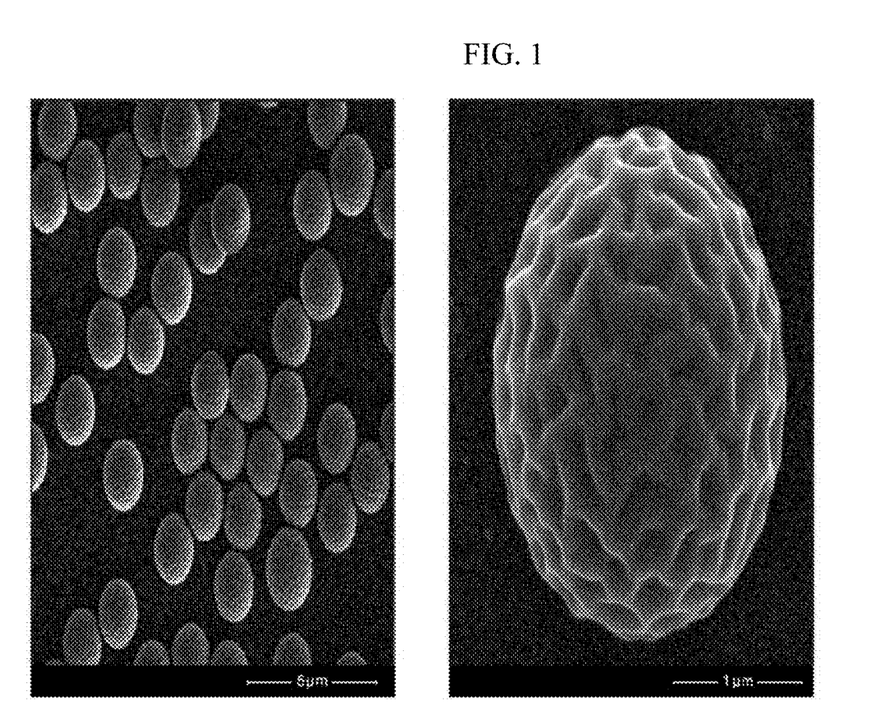
FIG. 1 is a scanning electron microscope (SEM) image of polymethylsilsesquioxane (PMSQ) having a wrinkled surface according to the present disclosure.

FIG. 1 shows particles of polymethylsilsesquioxane according to an embodiment.

In FIG. 1, particles of polymethylsilsesquioxane have a wrinkled surface.

Figure 2:
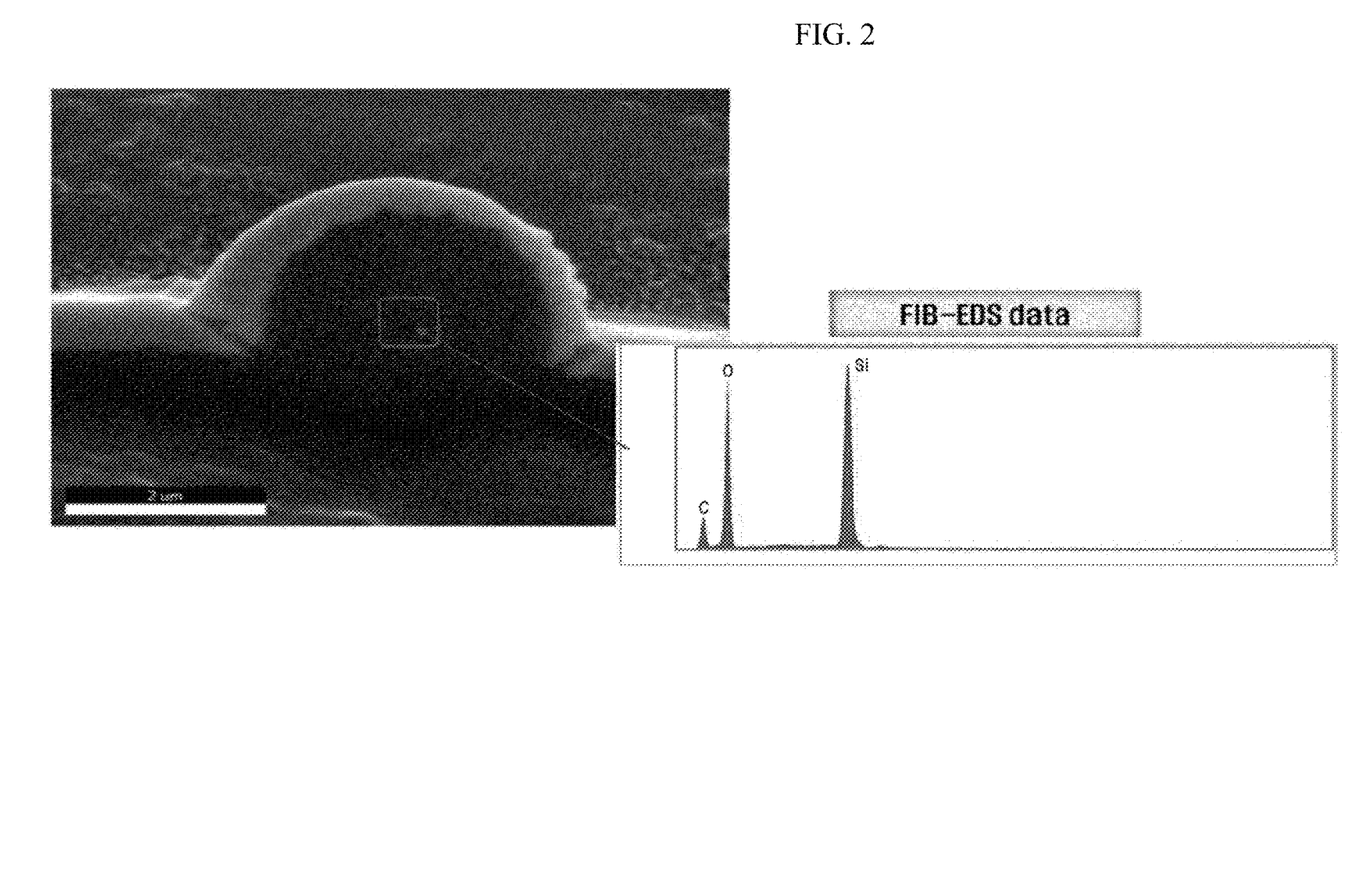
FIG. 2 is a focused loan beam (FIB) image of polymethylsilsesquioxane (PMSQ) having a wrinkled surface according to the present disclosure.

FIG. 2 is a focused loan beam (FIB) image of polymethylsilsesquioxane.

The FIB image of polymethylsilsesquioxane in FIG. 2 shows that in particles of polymethylsilsesquioxane, Si, O and C are included. The particles of polymethylsilsesquioxane comprise Si, O, and C, include a hydroxyl ion (—OH) and has wrinkled surfaces. Thus, the component polymethylsilsesquioxane may ensure excellent water absorbability and oil absorbability.

The component polymethylsilsesquioxane having a wrinkled surface may be prepared through a reaction between a silicone monomer and two or more basic catalysts. Additionally, a speed of the reaction between the silicone monomer and the two or more basic catalysts may be adjusted in various ways. When the silicone monomer reacts with the two or more basic catalysts and a speed of the reaction is adjusted in various ways, the component polymethylsilsesquioxane having a wrinkled surface may be prepared.

A diameter of a particle of the prepared component polymethylsilsesquioxane having a wrinkled surface may be 2 to 5 µm. Additionally, acidity of the component polymethylsilsesquioxane having a wrinkled surface may be pH 6 to 9 on the basis of 10% of an aqueous dispersion liquid. Further, maximum moisture content of the component polymethylsilsesquioxane having a wrinkled surface may be 1 to 3% at about 130° C. for two hours.

At least one coating layer may be formed on the surface of polymethylsilsesquioxane. The coating layer may include one or more of a metal oxide, a metal hydroxide, a dye and a pigment.

When the component polymethylsilsesquioxane, provided with the coating layer onto the surface thereof, is applied to cosmetics, adherence of the cosmetics to the skin may be improved, a skin tone may be improved, and skin flaws may be covered up/removed. Further, when polymethylsilsesquioxane, provided with multiple coating layers onto the surface thereof, is applied to cosmetics, excellent dispersibility may be ensured, thereby improving stability of products.

The metal oxide may denote various types of metal compounds to which oxygen is bonded. The metal oxide may include one or more of titanium dioxide ($TiO_2$), zinc oxide (ZnO), iron oxide ($Fe_2O_3$), tin oxide ($SnO_2$), zirconium dioxide ($ZrO_2$), silicon dioxide ($SiO_2$), aluminum oxide ($Al_2O_3$), magnesium oxide (MgO) and manganese dioxide ($MnO_2$). For the metal oxide, two or more of the metal oxides may be compound and used to prevent discoloration and to improve gloss.

The metal hydroxide may denote metal compounds where metallic salts and a hydroxyl group are bonded. The metal hydroxide may include alkali metal hydroxides. The alkali metal hydroxides may be prepared using a metal chloride and an alkaline solution. The metal chloride may not be limited and may include tin chloride ($SnCl_4$), titanium oxy chloride ($TiOCl_2$), zirconium oxy chloride ($ZrOCl_2$), silicon tetra chloride ($SiCl_4$), aluminum chloride ($AlCl_3$), magnesium chloride ($MgCl_2$) and manganese chloride ($MnCl_2$). The alkali metal hydroxide may be prepared by mixing two or more of the metal chlorides, and the alkaline solution.

The dye may include one or more of natural dyes of red series, blue series, green series, purple series, yellow series and black series. For example, materials of nature dyes of red series or purple series may be at least one selected from madders, safflowers, sappanwood, logwood, gromwells, persimmons, apricot trees, Japanese apricot trees, Korean spindle trees, Korean spice bushes, ginger roots, hollyhocks, Asiatic knotweeds, yews, schisandra fruits, camellias, grapes, birches, and combinations thereof. Additionally, materials of nature dyes of yellow series or green series may be at least one selected from gardenias, tumerics, onion skin, Carthamus yellow, barberry roots, phellodendron bark, cloves, pomegranates, common reeds, sophora flowers, ash trees, lacquer trees, wax trees, wild pear trees, forsythia tree bark, sesames, alder trees, chestnut trees, sawtooth oaks and combinations thereof.

The pigment may include one or more of a natural pigment, a gloss pigment where the natural pigment is coated on the metal oxide, and a gloss pigment where the natural pigment is coated on the metal hydroxide. For example, the natural pigment may be a vegetable pigment.

The pigment may be a gloss pigment where the natural pigment is coated on the metal oxide including one or more of titanium dioxide ($TiO_2$), zinc oxide (ZnO), iron oxide ($Fe_2O_3$), tin oxide ($SnO_2$), zirconium dioxide ($ZrO_2$), silicon dioxide ($SiO_2$), aluminum oxide ($Al_2O_3$), magnesium oxide (MgO) or manganese dioxide ($MnO_2$). Additionally, the pigment may be a gloss pigment where the natural pigment is coated on the alkali metal hydroxide.

Further, the pigment may include a pigment such as carmine and Ferric ferrocyanide, for example. Accordingly, the cosmetics composition according to the present disclosure may include color pigments.

A coating layer including one or more of metal oxides and metal hydroxides may be formed on the surface of the component polymethylsilsesquioxane. Accordingly, when the component polymethylsilsesquioxane is applied to cosmetics, the effects of metallic luster and interference color may be produced.

The component polymethylsilsesquioxane may be treated with a surface treatment agent. The surface treatment agent may include one or more of silicone oil (methicone, dimethicone, triethoxycaprylylsilane and the like), metallic soap (aluminum dimyristate, aluninum stearate, magnesium myristate and the like), fatty acids (stearic acids, myristic acids, isostearic acids and the like), lecithin, amino acids and wax.

The surface of the component polymethylsilsesquioxane may be treated with the above-describe surface treatment agents. Accordingly, when the component polymethylsilsesquioxane is applied to color cosmetics, dispersibility may be improved. Additionally, as the component may be mixed as even particles, adherence of the component to the skin may be improved, and skin may be moisturized and may be prevented from becoming dry.

A cosmetics composition including silicone powders having a wrinkled surface is described hereunder.

Cosmetics formulated with the cosmetics composition may include silicone powders. They may have improved sweat absorbability and sebum absorbability. Accordingly, the cosmetics may have excellent persistence of make-up and a light feeling of application. In addition, they cause no oiliness and stickiness, after they are applied to the skin.

Relative to the total wt % of the cosmetics composition, 1 to 15 wt % of polymethylsilsesquioxane (PMSQ) may be included. For example, relative to the total wt % of the cosmetics composition, 2 to 10 wt % of polymethylsilsesquioxane (PMSQ) may be included. However, in case the cosmetics composition is used for non-compressed products such as loose powders, content of polymethylsilsesquioxane (PMSQ) may not be limited.

In case less than 1 wt % of polymethylsilsesquioxane is included relative to the total wt % of the cosmetics composition, cosmetics formulated with the cosmetics composition may have degraded sweat absorbability and sebum absorbability. Additionally, when cosmetics formulated with the cosmetics composition are applied to the skin, persistence of make-up may not be ensured due to unabsorbed sweat and sebum. When cosmetics formulated with the cosmetics composition are applied to the skin, a skin tone becomes dull, and the skin becomes oily and sticky. When cosmetics formulated with the cosmetics composition are applied to the skin, skin flaws may not be covered, and a light feeling of application may not be ensured.

In case more than 15 wt % of polymethylsilsesquioxane is included relative to the total wt % of the cosmetics composition, cosmetics formulated with the cosmetics composition may have high viscosity and a heavy feeling of application. In addition, mouldibility of the cosmetics composition may be degraded and manufacturing costs may increase.

Accordingly, when 1 to 15 wt % of polymethylsilsesquioxane (PMSQ) is included relative to the total wt % of the cosmetics composition according to the present disclosure, cosmetics formulated with the cosmetics composition may ensure persistence of make-up and keeping the skin from looking dull. Additionally, cosmetics formulated with the cosmetics composition may improve a feeling of application and prevent a deterioration of mouldability.

The cosmetics composition according to the present disclosure may be one or more formulations selected from a group consisting of ointment, paste, cream, gel, powder, spray, liquid, emulsion, suspension, soap, shampoo and rinse.

The cosmetics composition according to the present disclosure may be one or more formulations selected from a group consisting of BB creams, foundations, make-up bases, primers, skin covers, powder pacts, two-way cakes, loose powders, eye shadows, eyeliners, mascaras, eyebrow products, blushers, highlighters, shading cosmetics, lipsticks, lip glosses, lip tints, lip balms, lip lacquers, liquid rouges, sun creams, toners, emulsions, creams, essences, ampoules, mists and cleansing foams.

The cosmetics composition according to the present disclosure may include one or more compositions that are mixed with ordinary cosmetics materials and that are allowable from a cosmetology perspective. For example, the composition mixed to ordinary materials for cosmetics may include oil, water, a surfactant, a moisturizer, low alcohol, a thickener, a chelating agent, a pigment, a preservative, a fragrance and the like properly, but not limited.

The composition mixed to ordinary materials for cosmetics may vary depending on formulations.

In case a formulation according to the present disclosure is ointment, paste, cream or gel, animal fats, vegetable oils, wax, paraffin, starch, tragacanth, cellulose derivative, polyethylene glycol, silicone, bentonite, silica, talc, zinc oxide or combinations thereof may be used as the composition.

In case a formulation according to the present disclosure is powder or spray, lactose, talc, aluminum hydroxide, calcium silicate, polyamide powder or combinations thereof may be used as the composition. In case a formulation according to the present disclosure is spray, a propellant such as chlorofluorohydrocarbon, propane/butane or dimethyl ether may be additionally included.

In case a formulation according to the present disclosure is solution or emulsion, a solvent, a solubilizer, or a demulsifier may be used as the composition. For example, water, ethanol, isopropanol, ethyl carbonate, ethyl acetate, benzyl alcohol, benzyl benzoate, propylene glycol, and 1,3-butyl glycol oil may be used as the composition. Particularly, cotton seed oil, peanut oil, corn seed oil, olive oil, castor oil and sesame oil, glycerol aliphatic ester, polyethylene glycol, or sorbitan fatty acid ester may be used as the composition.

In case a formulation according to the present disclosure is a suspension, a liquid-phase diluent such as water, ethanol or propylene glycol, a suspension such as ethoxylated isostearyl alcohol, polyoxyethylene sorbitol ester, polyoxyethylene sorbitan ester, micro crystalline cellulose, aluminum metahydroxide, bentonite, agar or tragacanth and the like may be used as the composition.

In case a formulation according to the present disclosure is soap, shampoo or rinse, fatty acid alkali metallic salt, fatty acid hemiester salt, fatty acid protein hydrolysate, isethionate, lanoline derivative, aliphatic alcohol, vegetable oil, glycerol, sugar and the like may be used as the composition.

Examples are described hereunder with reference to embodiments according to the present disclosure and the like. However, the present disclosure is not intended to limit the below-described embodiments.

EMBODIMENT

<Preparation Example 1> PMSQ Having Wrinkled Surface

Sodium hydroxide (NaOH), which is an alkaline solution, was added to a silicone monomer to increase a reaction speed, and ammonium hydroxide ($NH_4OH$) was added to the silicone monomer to decrease the reaction speed. Then polymethylsilsesquioxane powders having a wrinkled surface were prepared.

<Preparation Example 2> Coating Wrinkled Surface of PMSQ with Metal Hydroxide

Polymethylsilsesquioxane powders, prepared based on preparation example 1, and water were added and agitated at a speed of 400 rpm at about 70° C. to prepare a suspension. Then acids were added to the suspension. Acidity of the suspension, to which acids were added, was in a range of pH 1 to 3. Next, a metal chloride ($SnCl_4$) and the alkaline solution (NaOH) were added to the suspension. A coating layer of Sn(OH)$_4$ was formed on surfaces of polymethylsilsesquioxane particles. Then a metal chloride (TiOCl$_2$) and the alkaline solution (NaOH) were added to the coating layer. A coating layer of Ti(OH)$_4$ was formed on top of the coating layer of Sn(OH)$_4$ on the surfaces of polymethylsilsesquioxane particles.

<Preparation Example 3> Coating Wrinkled Surface of PMSQ with Metal Oxide

The powders of polymethylsilsesquioxane, where the coating layers were formed based on preparation example 2, were calcinated at about 400 to 500° C. for 20 to 30 minutes. A coating layer of TiO$_2$ was formed on top of a coating layer of SnO$_2$ was formed on the surfaces of polymethylsilsesquioxane particles.

<Preparation Example 4> Surface-Treating Wrinkled Surface of PMSQ

Polymethylsilsesquioxane powders, prepared based on preparation example 1, and dimethicone were mixed. The surface of polymethylsilsesquioxane was treated with dimethicone.

<Preparation Example 5> Coating Wrinkled Surface of PMSQ with Natural Pigment Polymethylsilsesquioxane powders, prepared based on preparation example 1, and 1 l of water were added and dispersed at a speed of 400 rpm to prepare a suspension. Next, a sappanwood pigment and CaCl$_2$) were put into the suspension, and acidity of the mixed solution was adjusted to pH 5. Then polymethylsilsesquioxane powders were rinsed and dehydrated while being agitated for about ten minutes, and then dried at 80° C. Thus, a coating layer of the red sappanwood pigment was formed on the surfaces of polymethylsilsesquioxane particles.

Embodiment 1

A diameter of the particle was 3 μm and 10 wt % of polymethylsilsesquioxane powders having a wrinkled surface was used.

Comparative Example 1

Polymethylsilsesquioxane powders of GE Toshiba Silicones having a smooth surface were used. A diameter of a particle of polymethylsilsesquioxane powders was 6 μm and 10 wt % of polymethylsilsesquioxane powders were used.

Comparative Example 2

Polymethylsilsesquioxane powders of Shin-Etsu Silicones having a smooth surface were used. A diameter of a particle of polymethylsilsesquioxane powders was 5 μm and 10 wt % of polymethylsilsesquioxane powders were used.

<Embodiment 2>, <Comparative Example 3> Applying PMSQ Prepared Based on Preparation Example 1 to BB Cream

TABLE 1

Composition of BB cream

| Group | Component | Embodiment 2 (wt %) | Comparative example 3 (wt %) |
|---|---|---|---|
| A | Purified water | Bal. | Bal. |
|  | Glycerin | 4.00 | 4.00 |
|  | Butylene glycol | 4.00 | 4.00 |
| B | Beeswax | 1.50 | 1.50 |
|  | Dimethicone | 18.00 | 18.00 |
|  | PEG-10 Dimethicone | 4.00 | 4.00 |
|  | Caprlic/Capric triglyceride | 7.00 | 7.00 |
|  | Isododecane/Distearcimonium hectorite/Propylene carbonate | 2.00 | 2.00 |
|  | Phenyl trimethicone | 7.00 | 7.00 |
|  | Preservative | 0.30 | 0.30 |
| C | Iron oxide (surface-treated with methicone) | 1.00 | 1.00 |
|  | Polymethyl methacrylate | 1.00 | 1.00 |
|  | Titanium dioxide (surface-treated with methicone) | 5.00 | 5.00 |
|  | Zinc oxide (surface-treated with methicone) | 2.00 | 2.00 |
|  | Polymethylsilsesquioxane (PMSQ) having wrinkled surface prepared based on preparation example 1 | 5.00 | — |

Components of group B in table 1 above were evenly mixed at 80° C. Next, components of group C were evenly mixed, then added to the components of group B, and then dispersed evenly. Next, components of group A were emulsified for 10 minutes while being added slowly to the components of group B and group C at 80° C. using a homogenizer, and then cooled up to 30° C. Thus, a BB cream was manufactured.

<Embodiment 3>, <Comparative Example 4> Applying PMSQ Prepared Based on Preparation Example 1 to Pressed Powder

TABLE 2

Composition of pressed powder

| Group | Component | Embodiment 3 (wt %) | Comparative example 4 (wt %) |
|---|---|---|---|
| A | Talc | Bal. | Bal. |
|  | Sericite | 20.00 | 20.00 |
|  | Mica | 5.00 | 5.00 |
|  | Magnesium stearate | 5.00 | 5.00 |
|  | Polymethylsilsesquioxane (PMSQ) having wrinkled surface prepared based on preparation example 1 | 10.00 | — |
| B | Iron oxide | 3.00 | 3.00 |
| C | Caprlic/Capric triglyceride | 4.00 | 4.00 |
|  | Isotridecyl isononanoate | 3.00 | 3.00 |
|  | Dimethicone | 3.00 | 3.00 |
|  | Preservative | 0.30 | 0.30 |

Components of group A and group B in table 2 were weighed and then mixed evenly for one minute using a mixer. Next, components of group C were added to the components of group A and group B and then mixed evenly for one minute using the mixer. Next, a proper amount of the mixed half product was put into a mould and moulded using a compression moulding machine. Thus, a pressed powder was manufactured.

<Embodiment 4>, <Comparative Example 5>
Applying PMSQ Prepared Based on Preparation Example 1 to Sun Cream

TABLE 3

Composition of sun cream

| Group | Component | Embodiment 4 (wt %) | Comparative example 5 (wt %) |
|---|---|---|---|
| A | Purified water | Bal. | Bal. |
| | Glycerin | 4.00 | 4.00 |
| | Butylene glycol | 8.00 | 8.00 |
| B | Beeswax | 1.00 | 1.00 |
| | Cyclopentasiloxane | 15.00 | 15.00 |
| | PEF-10 Dimethicone | 4.00 | 4.00 |
| | Ethylhexyl methoxycinnamate | 7.00 | 7.00 |
| | Isododecane/Disteardimonium hectorite/Propylene carbonate | 2.00 | 2.00 |
| | Dimethicone | 7.00 | 7.00 |
| | Preservative | 0.30 | 0.30 |
| C | Polymethylsilsesquioxane (PMSQ) having wrinkled surface prepared based on preparation example 1 | 5.00 | — |
| | Titanium dioxide (surface-treated with methicone) | 5.00 | 5.00 |
| | Zinc oxide (surface-treated with methicone) | 3.00 | 3.00 |

Components of group B in table 3 were mixed evenly at 80° C. Next, components of group C were mixed evenly, then added to the components of group B and then dispersed evenly. Next, components of group A were emulsified for 10 minutes while being added slowly to the components of group B and group C at 80° C. using the homogenizer, and then cooled up to 30° C. Thus, a sun cream was manufactured.

<Embodiment 5>, <Comparative Example 6>
Applying PMSQ Prepared Based on Preparation Example 1 to Emulsion

TABLE 4

Composition of emulsion

| Group | Component | Embodiment 5 (wt %) | Comparative example 6 (wt %) |
|---|---|---|---|
| A | Purified water | Bal. | Bal. |
| | Carbomer | 0.40 | 0.40 |
| B | Glycerin | 10.00 | 10.00 |
| | Butylene glycol | 5.00 | 5.00 |
| | Sodium chloride | 0.50 | 0.50 |
| C | Cetyl alcohol | 1.00 | 1.00 |
| | Beeswax | 1.00 | 1.00 |
| | Caprlic/Capric triglyceride | 7.00 | 7.00 |
| | Dimethicone | 2.00 | 2.00 |
| | Sorbitan sesquioleate | 0.80 | 0.80 |
| | polysorbate 80 | 2.00 | 2.00 |
| | Preservative | 0.50 | 0.50 |
| D | Polymethylsilsesquioxane (PMSQ) having wrinkled surface prepared based on preparation example 1 | 5.00 | — |

Components of group A in table 4 were weighed and then dispersed evenly at 70° C. Next, components of group B were added to the components of group A and then mixed evenly for five minutes. Next, components of group C were emulsified for 10 minutes while being added slowly to the components of group A and group B at 70° C. using the homogenizer. Next, in embodiment 5, the emulsified components were cooled up to 40° C., and then components of group D were added, emulsified for five minutes and then cooled up to 30° C. to manufacture an emulsion. In comparative example 6, the components of group D were not added, and the emulsified components were cooled up to 30° C. to manufacture an emulsion.

<Embodiment 6>, <Comparative Example 7>
Applying PMSQ Prepared Based on

Preparation Example 3 to Emulsion

TABLE 5

Composition of emulsion

| Group | Component | Embodiment 6 (wt %) | Comparative example 7 (wt %) |
|---|---|---|---|
| A | Purified water | Bal. | Bal. |
| | Carbomer | 0.40 | 0.40 |
| B | Glycerin | 10.00 | 10.00 |
| | Butylene glycol | 5.00 | 5.00 |
| | Sodium chloride | 0.50 | 0.50 |
| C | Cetyl alcohol | 1.00 | 1.00 |
| | Beeswax | 1.00 | 1.00 |
| | Caprlic/Capric triglyceride | 6.00 | 6.00 |
| | Dimethicone | 3.00 | 3.00 |
| | Sorbitan sesquioleate | 1.00 | 1.00 |
| | Polysorbate 80 | 2.20 | 2.20 |
| | Preservative | 0.50 | 0.50 |
| D | Polymethylsilsesquioxane (PMSQ) having wrinkled surface prepared based on preparation example 3 | 5.00 | — |

Components of group A in table 5 were weighed and then dispersed evenly at 70° C. Next, components of group B were added to the components of group A and then mixed evenly for five minutes. Next, components of group C were emulsified for 10 minutes while being added slowly to the components of group A and group B at 70° C. using the homogenizer. Next, in embodiment 6, the emulsified components were cooled up to 40° C., and then components of group D were added, emulsified for five minutes and then cooled up to 30° C. to manufacture an emulsion. In comparative example 7, the components of group D were not added, and the emulsified components were cooled up to 30° C. to manufacture an emulsion.

<Embodiment 7>, <Comparative Example 8>
Applying PMSQ Prepared Based on

Preparation Example 4 to Pressed Powder

TABLE 6

Composition of pressed powder

| Group | Component | Embodiment 7 (wt %) | Comparative example 8 (wt %) |
|---|---|---|---|
| A | Talc | Bal. | Bal. |
|  | Sericite | 20.00 | 20.00 |
|  | Mica | 5.00 | 5.00 |
|  | Magnesium stearate | 5.00 | 5.00 |
|  | Polymethylsilsesquioxane (PMSQ) having wrinkled surface prepared based on preparation example 4 | 10.00 | — |
| B | Iron oxide | 3.00 | 3.00 |
| C | Caprlic/Capric triglyceride | 4.00 | 4.00 |
|  | Isotridecyl isononanoate | 3.00 | 3.00 |
|  | Dimethicone | 3.00 | 3.00 |
|  | Preservative | 0.30 | 0.30 |

Components of group A and group B in table 6 were weighed and then mixed evenly for one minute using the mixer. Next, components of group C were added to the components of group A and group B and then mixed evenly for one minute using the mixer. Next, a proper amount of the mixed half product was put into a mould and moulded using a compression moulding machine. Thus, a pressed powder was manufactured.

Experimental Example

1. Measurement of Amount of Absorbed Sebum and Sweat

TABLE 7

Composition of sample similar to sebum

| Component | Amount (wt %) |
|---|---|
| Caprlic/Capric triglyceride | 50.00 |
| Squalene | 12.00 |
| Jojoba oil | 36.40 |
| Beeswax | 0.20 |
| Candelillia wax | 0.20 |
| Carnauba wax | 0.20 |
| 7-Dihydrocholesterol | 1.00 |
| TOTAL | 100.00 |

Components of sebum include 50% of triglycerides, 10% of free fatty acids, 12% of squalene, 25% of wax esters, 1% of cholesterol, linoleic acids and the remaining components. Components and composition ratio of the components and composition ratio of the sample similar to sebum in table 7 above are similar to the components and composition ratio of sebum. Oil absorbability regarding sebum of polymethylsilsesquioxane (PMSQ) in embodiment 1 and polymethylsilsesquioxane (PMSQ) in comparative examples 1 and 2 was evaluated using the sample similar to sebum. Table 9 below shows results of the evaluation.

Additionally, sweat is composed of 99% of water, and the remaining 1% contains sodium, chlorine, potassium, nitrogen inclusions, lactic acids, urea and the like. Concentration of sodium ranges from 0.4% to 1%. Accordingly, water absorbability regarding sweat of polymethylsilsesquioxane (PMSQ) in embodiment 1 and polymethylsilsesquioxane (PMSQ) in comparative examples 1 and 2 was evaluated using saline solution (0.9% of sodium concentration) having a sodium concentration similar to that of sweat. Table 8 below shows results of the evaluation.

TABLE 8

Result of measurement of amount of absorbed oil and water

|  | Component | Polymethylsilsesquioxane (PMSQ) of embodiment 1 | Polymethylsilsesquioxane (PMSQ) in comparative example 1 | Polymethylsilsesquioxane (PMSQ) in comparative example 2 |
|---|---|---|---|---|
| Amount of absorbed oil (g/100 g) | Sample similar to sebum | 106.5 | 91.5 | 81.0 |
| Amount of absorbed water (g/100 g) | Saline solution | 65.3 | Impossible to measure | Impossible to measure |

As a result of measurement of an amount of absorbed oil using the sample similar to sebum as in table 8, the amount of absorbed oil of polymethylsilsesquioxane (PMSQ) in embodiment 1 was 106.5 g/100 g; 91.5 g/100 g in comparative example 1; 81.0 g/100 g in comparative example 2. As polymethylsilsesquioxane (PMSQ) in embodiment 1 has a wrinkled surface, the amount of absorbed oil of polymethylsilsesquioxane (PMSQ) in embodiment 1 was larger than that of polymethylsilsesquioxane (PMSQ) in comparative examples 1 and 2. Additionally, as a result of measurement of an amount of absorbed water using saline solution that is a sample similar to sweat, the amount of absorbed water of polymethylsilsesquioxane (PMSQ) in embodiment 1 was 65.3 g/100 g. However, as polymethylsilsesquioxane (PMSQ) in comparative examples 1 and 2 has a high water repellency and no water absorbability, the amount of absorbed water of polymethylsilsesquioxane (PMSQ) in comparative examples 1 and 2 could not be measured. Thus, polymethylsilsesquioxane (PMSQ) in embodiment 1 has water absorbability as well as oil absorbability since polymethylsilsesquioxane (PMSQ) in embodiment 1 has a wrinkled surface.

2. Evaluation of Dispersibility of Oil and Water

Figure 3:
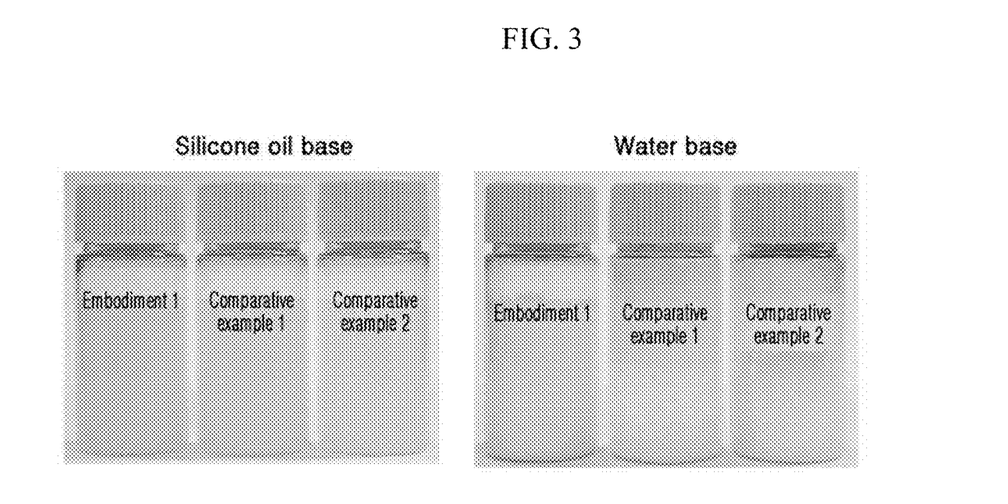
FIG. 3 is an image illustrating dispersion properties of polymethylsilsesquioxane (PMSQ) of embodiment 1, and polymethylsilsesquioxane (PMSQ) of comparative examples 1 and 2 in a silicone oil base and in a water base.

Polymethylsilsesquioxane (PMSQ) in embodiment 1 and polymethylsilsesquioxane (PMSQ) in comparative examples 1 and 2 were dispersed in a silicone oil base and in water. FIG. 3 below shows results of the dispersion.

Polymethylsilsesquioxane (PMSQ) in embodiment 1 and polymethylsilsesquioxane (PMSQ) in comparative examples 1 and 2 were all dispersed smoothly in the silicone oil base. However, polymethylsilsesquioxane (PMSQ) in embodiment 1 was only dispersed in water.

Polymethylsilsesquioxane (PMSQ) in embodiment 1 and polymethylsilsesquioxane (PMSQ) in comparative examples 1 and 2 all absorbed oil. However, polymethylsilsesquioxane (PMSQ) having no wrinkled surface in comparative examples 1 and 2 did not absorb water. Accordingly, polymethylsilsesquioxane (PMSQ) in comparative examples 1 and 2 had a low dispersibility in water.

3. Evaluation of Quality of Cosmetics

Resistance against sweat, resistance against sebum, a feeling of application, stickiness and greasiness of cosmetics compositions in embodiments 2 to 5 and in comparative examples 3 to 6 were evaluated. Additionally, resistance against sweat, resistance against sebum, a light feeling of application, adherence and improvement in skin tone of cosmetics compositions in embodiment 6 and in comparative example 7 were evaluated. Further, resistance against sweat, resistance against sebum, a light feeling of application, adherence and moisture levels of cosmetics compositions in embodiment 7 and in comparative example 8 were evaluated.

As a test panel, twenty female consumers aged between 20 to 40 used the cosmetics composition/products including the cosmetics composition for 15 days and graded the cosmetics composition/products including the cosmetics composition on the basis of a 1 to 5 point grading system. Then an average of points was calculated. Table 9 to 11 below shows results of the calculation.

[Grade]
1: Poor 2: Fair 3: Good 4: Very good 5: Excellent

TABLE 9

| | Resistance (sweat) | Resistance (oil) | Feeling of application | Stickiness | Greasiness |
|---|---|---|---|---|---|
| Embodiment 2 | 4.2 | 4.8 | 4.4 | 4.3 | 4.5 |
| Comparative example 3 | 3.2 | 3.3 | 3.1 | 2.9 | 3.4 |
| Embodiment 3 | 4.4 | 4.5 | 4.8 | 4.7 | 4.6 |
| Comparative example 4 | 3.4 | 3.1 | 2.9 | 3.0 | 3.0 |
| Embodiment 4 | 4.1 | 4.4 | 4.5 | 4.5 | 4.4 |
| Comparative example 5 | 3.5 | 3.6 | 3.0 | 2.8 | 3.1 |
| Embodiment 5 | 4.2 | 4.8 | 4.7 | 4.8 | 4.8 |
| Comparative example 6 | 3.5 | 3.6 | 2.9 | 2.6 | 3.2 |

Table 9 shows that a BB cream, a pressed powder, a sun cream and an emulsion including polymethylsilsesquioxane (PMSQ) having a wrinkled surface in embodiments 2 to 5 may prevent dull skin (skin darkening) caused by sebum and sweat and may improve persistence. Additionally, polymethylsilsesquioxane (PMSQ) having a wrinkled surface is very soft powder and has oil absorbability and water absorbability. Accordingly, the component polymethylsilsesquioxane (PMSQ) may ensure a light application feeling, may reduce stickiness or oiliness and may provide a natural look to users.

TABLE 10

| | Resistance (sweat) | Resistance (oil) | Feeling of application | Adherence | Improvement in skin tone |
|---|---|---|---|---|---|
| Embodiment 6 | 4.1 | 4.7 | 4.1 | 4.3 | 4.2 |
| Comparative example 7 | 3.2 | 3.3 | 3.1 | 2.9 | 2.5 |

Table 10 shows that an emulsion including polymethylsilsesquioxane (PMSQ) having a wrinkled surface coated with a metal oxide in embodiment 6 prevented dull skin (skin darkening) caused by sebum and sweat and improved persistence. Additionally, polymethylsilsesquioxane (PMSQ) having a wrinkled surface is very soft powder and ensures excellent adherence and improvement in skin tone.

TABLE 11

| | Resistance (sweat) | Resistance (oil) | Feeling of application | Adherence | Moisture level |
|---|---|---|---|---|---|
| Embodiment 7 | 4.1 | 4.7 | 4.1 | 4.3 | 4.2 |
| Comparative example 8 | 3.2 | 3.3 | 3.1 | 2.9 | 2.5 |

Table 11 shows that a pressed powder including polymethylsilsesquioxane (PMSQ) having a surface-treated wrinkled surface in embodiment 7 prevented dull skin (skin darkening) caused by sebum and sweat and improved persistence. Additionally, polymethylsilsesquioxane (PMSQ) having a wrinkled surface is very soft powder, ensures excellent adherence and increases moisture levels.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art. Thus, the embodiments are provided only as examples and are not limited.

The invention claimed is:

1. A cosmetics composition having improved water absorbability and oil absorbability, comprising:
   a silicone particle, wherein the silicone particle is substantially spherical, and the silicone particle has a plurality of grooves and ridges on a surface thereof; and
   a coating layer on the surface of the silicone particle, wherein the coating layer comprises a metal hydroxide, and the coating layer is formed by depositing the metal hydroxide on the surface of the silicone particle.

2. The cosmetics composition of claim 1, wherein the silicone particle comprises polymethylsilsesquioxane (PMSQ).

3. The cosmetics composition of claim 1, wherein the coating layer further comprises at least one selected from the group consisting of a dye and a pigment.

4. The cosmetics composition of claim 1, wherein the metal hydroxide is deposited on the surface of the silicone particle from a metal compound in which a metallic salt and a hydroxyl group are bonded.

5. The cosmetics composition of claim 3, wherein the coating layer comprises the dye, and wherein the dye comprises at least one selected from the group consisting of a red series dye, a blue series dye, a green series dye, a purple series dye, a yellow series dye, and a black series dye.

6. The cosmetics composition of claim 3, wherein the coating layer comprises the pigment, and the pigment comprises at least one selected from the group consisting of carmine and ferric ferrocyanide.

7. The cosmetics composition of claim 2, wherein the cosmetics composition includes 1 to 15 wt % of the component polymethylsilsesquioxane (PMSQ) relative to a total wt % of the cosmetics composition.

8. The cosmetics composition of claim 2, wherein the component polymethylsilsesquioxane (PMSQ) is treated with a surface treatment agent.

9. The cosmetics composition of claim 8, wherein the surface treatment agent includes one or more of silicone oil, metallic soap, fatty acids, lecithin, amino acids, and wax.

10. The cosmetics composition according to claim 1, wherein the cosmetics composition is one or more formulations selected from a group consisting of ointment, paste, cream, gel, powder, spray, liquid, emulsion, suspension, soap, shampoo and rinse.

11. A cosmetics composition having improved water absorbability and oil absorbability, comprising:
a silicone particle, wherein the silicone particle is substantially spherical, and the silicone particle has a plurality of grooves and ridges on a surface thereof; and
a coating layer on the surface of the silicone particle, wherein the coating layer comprises a metal oxide, and the coating layer is formed by depositing a metal hydroxide on the surface of the silicone particle, and calcinate the silicone particle and the deposited metal hydroxide to produce the metal oxide.

12. The cosmetics composition of claim 11, wherein the silicone particle comprises a calcination product of polymethylsilsesquioxane (PMSQ).

13. The cosmetics composition of claim 11, wherein the metal oxide comprises at least one selected from the group consisting of titanium dioxide ($TiO_2$), zinc oxide (ZnO), iron oxide ($Fe_2O_3$), tin oxide ($SnO_2$), zirconium dioxide ($ZrO_2$), silicon dioxide ($SiO_2$), aluminum oxide ($Al_2O_3$), magnesium oxide (MgO) and manganese dioxide ($MnO_2$).

* * * * *